US008420344B2

(12) United States Patent
Shearer et al.

(10) Patent No.: US 8,420,344 B2
(45) Date of Patent: Apr. 16, 2013

(54) FATTY ACID PATTERN ANALYSIS FOR PREDICTING ACUTE CORONARY SYNDROME

(75) Inventors: Gregory C. Shearer, Sioux Falls, SD (US); James V. Pottala, Sioux Falls, SD (US); William S. Harris, Sioux Falls, SD (US)

(73) Assignee: Integrated Health Leaders, LLC, Richmond, VA (US)

( * ) Notice: Subject to any disclaimer, the term of this patent is extended or adjusted under 35 U.S.C. 154(b) by 114 days.

(21) Appl. No.: 12/421,784

(22) Filed: Apr. 10, 2009

(65) Prior Publication Data

US 2010/0021956 A1 Jan. 28, 2010

Related U.S. Application Data

(60) Provisional application No. 61/135,822, filed on Jul. 23, 2008.

(51) Int. Cl.
*C12Q 1/02* (2006.01)
*C12Q 1/00* (2006.01)

(52) U.S. Cl.
USPC ................................................. 435/29; 435/4

(58) Field of Classification Search .................. 435/29, 435/4
See application file for complete search history.

(56) References Cited

PUBLICATIONS

Yi X.Y., Gauthier K.M., Lijie C, Nithipatikom K, Falck J.R. and Campbel W.B. Metabolism of adrenic acid to vasodilatory 1α,1β-dihomo-epoxyeicosatrienoic acids by bovine coronary arteries. American Journal of Physiology—Heart and Circulatory Physiology (2007) 292: H2265-H2274.*
D'Agostino R.B., Russell M.W., Huse D.M., Ellison R.C., Silbershatz H, Wilson P.W.F. and Hartz S.C. Primary and subsequent coronary risk appraisal: New results from The Framingham Study. American Heart Journal (2000) 139:272-281.*
Wang L., Folsom A.R., and Eckfeldt J.H. Plasma fatty acid composition and incidence of coronary heart disease in middle aged adults: The atherosclerosis Risk in Communities (ARIC) Study. Journal of Nutrition, Metabolism & Cardiovascular Diseases (2003) 13(5): 256-266.*
Lemaitre et al. (Plasma Phospholipid Trans Fatty Acids, Fatal Ischemic Heart Disease, and Sudden Cardiac Death in Older Adults: The Cardiovascular Health Study. Circulation 2006 (114) 209-215).*
Yli-Jama et al. (Serum free fatty acid pattern and risk of myocardial infarction: a case-control study. Journal of internal Medicine 2002: 251: 19-28).*
Hongtong et al. (Platelet Fatty Acids in Coronary Heart Disease, Dyslipidemia, Hypertension and Health Controls. Southeast Asian J Trop Med Public Health. 2003 34(3): 675-681).*
Wilson et al. (Prediction of Coronary Heart Disease Using Risk Factor Categories. Circulation 1998, 97: 1837-1847).*

Aarsetoey H, et al. The Journal of Nutrition. 2009; 139:1-7.
Aarsetoey, H, et al., Resuscitation. 2008. 78:258-264.
Albert CM, et al. The New England journal of medicine. 2002; 346(15):1113-1118.
Alpert JS, et al. Journal of the American College of Cardiology. 2000; 36(3):959-969.
Assmann G, et al. Circulation. 2002; 105(3):310-315.
Baylin, A, et al. Circulation. 2003; 107:1586-1591.
Baylin, A, et al. Journal of Nutrition. 2004; 134:3095-3099.
Block et al., Atherosclerosis Apr. 2008;197(2):821-8.
Block, et al., Am Heart J. 2008; 156:1117-23.
Braunwald E, et al. Journal of the American College of Cardiology. 2002;40(7):1366-1374.
Chambless LE, et al. Journal of clinical epidemiology. 2003; 56(9):880-890.
Clark, et al., British Journal of Nutrition. 2008; 1-6.
Clifton,et al., J. Nutr. 2004; 134:874-879.
Cook NR. Circulation. 2007; 115(7):928-935.
Cook NR. Clinical chemistry. 2008; 54(1):17-23.
De Backer G, et al. Atherosclerosis. 2004; 173(2):381-391.
Erkkila, et al. Am J Clin Nutr. 2003; 78:65-71.
Executive Summary of The Third Report of The National Cholesterol Education Program (NCEP) Expert Panel on Detection, Evaluation, and Treatment of High Blood Cholesterol In Adults (Adult Treatment Panel III). Jama. 2001; 285 (19):2486-2497.
Ferrucci L, et al. The Journal of clinical endocrinology and metabolism. 2006; 91(2):439-446.
Folsom AR, et al. Archives of internal medicine. 2006; 166(13):1368-1373.
German JB, et al. Current opinion in lipidology. 2007; 18(1):66-71.
Greenland P. et al. Statistics in medicine. 2008; 27(2):188-190.
Grewal J, et al. Atherosclerosis. 2008; 197(1):435-442.
Guallar, et al., JACC. 1995; 25(2): 387-94.
Guallar, et al., Arterioscler. Thromb. Vasc. Biol. 1999; 19:1111-1118.
Hallgren, et al., British Journal of Nutrition. 2001; 86:397-404.
Hanley JA, et al. Radiology. 1982; 143(1):29-36.
Hanley JA, et al. Radiology. 1983; 148(3):839-843.
Harris WS, et al. Atherosclerosis. 2007; 193(1):1-10.
Harris WS. Pharmacol Res. 2007; 55(3):217-223.
Harris WS. Current atherosclerosis reports. 2006; 8(6):453-459.
Harris WS, et al. Preventive medicine. 2004; 39(1):212-220.
Harris WS, et al. Current Cardiovascular Risk Reports. 2008; 2:161-166.
Harris, WS, et al., Am J Cardiol. 2007; 99:154-158.
Harris, WS, et al., Circulation. 2009; online.
Hino, A, et al., Atherosclerosis. 2004; 176:145-149.
Jurand J, et al. Atherosclerosis. 1970; 11(1):157-170.
Kaminskas, A, et al., Scandinavian Journal of Clinical Laboratory Investigation. 1999; 59(3):227-232.
Kardinaal, AFM, et al., Ateriosclerosis, Thrombosis, and Vascular Biology. 1995; 15:723-32.
Kark JD, et al. Journal of clinical epidemiology. 1995; 48(7):889-895.

(Continued)

*Primary Examiner* — Karen Cochrane Carlson
*Assistant Examiner* — Natalie Moss
(74) *Attorney, Agent, or Firm* — Jeffrey N. Townes; LeClairRyan (57) ABSTRACT

The present invention provides blood based methods for predicting risk of acute coronary syndrome in a subject.

16 Claims, 2 Drawing Sheets

PUBLICATIONS

Kark, JD, et al., Am J Clin Nutr. 2003; 77:796-802.
Kirkeby, K, et al., Acta Medica Scandinavica. 1972; 191:321-4.
Kirkeby, K, et al., Acta Medica Scandinavica. 1972; 192: 513-9.
Kondo, T, et al., Clinical Cardiology. 1986; 9:413-6.
Koshkin V, et al. The Journal of biological chemistry. 1998; 273(11):6046-6049.
Laaksonen, DE, et al., Arch Intern Med. 2005; 165:193-199.
Lands WE. The American journal of clinical nutrition. 1995; 61(3 Suppl):721S-725S.
Lanfear DE, et al. Jama. 2005; 294(12):1526-1533.
Lea, EJ, et al., Atherosclerosis.1982; 41:363-9.
Lemaitre, RN, et al., Circulation. 2002; 105:697-701.
Lemaitre, RN, et al., Am J Clin Nutr. 2003; 77:319-25.
Lemaitre, RN, et al., Circulation. 2006; 114:209-215.
Lemley KV. Pediatric nephrology (Berlin, Germany). 2007; 22(11):1849-1859.
Leng, GC, et al., Arteriosclerosis, Thrombosis, and Vascular Biology. 1994; 14:471-478.
Leng, GC, et al., Vascular Medicine. 1999; 4:219-226.
Lloyd-Jones DM, et al. Liu K, Tian L, Greenland P. Narrative Review: Assessment of C-Reactive Protein in Risk Prediction for Cardiovascular Disease. Annals of internal medicine. 2006.
Luostarinen, R, et al., Atherosclerosis. 1993; 99:187-93.
Ma DW, et al. The Journal of nutritional biochemistry. 2004; 15(11):700-706.
Maidment CG, et al. Atherosclerosis. 1988; 74(1-2):9-14.
Marcel YL, et al. Biochimica et biophysica acta. 1968; 164(1):25-34.
Marchioli R, et al. Circulation. 2002; 105(16):1897-1903.
Miettinen, TA, et al., British Medical Journal. 1982; 285:993-996.
Myerburg RJ, et al. Annals of internal medicine. 1993; 119(12):1187-1197.
Niu K, et al. The American journal of clinical nutrition. 2006; 84(1):223-229.
Oda, et al., Int Heart J. 2005; 46:583-591.
Oda, et al., Int Heart J. 2005; 46:975-985.
Paganelli, F. et al., International Journal of Cardiology. 2001; 78:27-32.
Pedersen, JI, et al., European Journal of Clinical Nutrition. 2000; 54:618-625.
Pencina MJ, et al. Statistics in medicine. 2008; 27(2):157-172.
Pepe MS, et al. American journal of epidemiology. 2004; 159(9):882-890.
Rissanen, T, et al., Circulation. 2000; 102:2677-2679.
Roberts, TL, et al., Heart.1993; 70:524-529.
Salonen, JT., et al., American Journal of Cardiology. 1985; 56:226-31.
Seidelin, KN, et al., Am J Clin Nutr.1992; 55:1117-9.
Siguel, EN, et al., Metabolism. 1994; 43:982-93.
Simon, et al., American Journal of Epidemiology. 1995; 142: 469-76.
Siscovick DS, et al. Jama. 1995; 274(17):1363-1367.
Skuladottir, G, et al., Acta Medica Scandinavica. 1985; 218:55-8.
Sun, et al., American Journal of Clinical Nutrition. 2008; 88:216-23.
Sundstrom, J, et al., Ciculation. 2001; 103:836-841.
Valek, J, et al., Atheroslcerosis.1985; 54: 111-8.
Valles, J, et al., Thrombosis Research. 1979; 14:231-4.
Vasan RS. Circulation. 2006; 113(19):2335-2362.
Wang C, et al. The American journal of clinical nutrition. 2006; 84(1):5-17.
Wang, Y, et al., Comparative Biochemistry and Physiology Part A.2003; 136:127-140.
Wenxun, F, et al., Am J Clin Nutr. 1990; 52:1027-36.
Willett WC. Atheroscler Suppl. 2006; 7(2):5-8.
Wilson PW, et al. Circulation. 1998; 97(18):1837-1847.
Wood, DA, et al., The Lancet. 1987; 329:177-83.
Yamagishi, K, et al., Am Heart J. 2008; 156:965-74.
Yli-Jama, P, et al., Journal of Internal Medicine. 2002; 251:19-28.
Ali et al., "Association between Omega-3 Fatty Acids and Depressive Symptoms among Patients with Established Coronary Artery Disease: Data from the Heart and Soul Study", Psychother. Psychosom. 78:125-27 (2009).
Amin et al., "Acute Coronary Syndrome Patients with Depression Have Low Blood Cell Membrane Omega-3 Fatty Acid Levels", Psychosom. Med. 70(8):856-62 (2008).
Bourre et al., "Dietary Omega-3 Fatty Acid and Psychiatry: Mood, Behaviour, Stress, Depression, Dementia and Aging", J. Nutrition, Health & Aging 9(1):31-8 (2005).
Edwards et al., "Omega-3 polyunsaturated fatty acid levels in the diet and in red blood cell membranes of depressed patients", J. Affective Disorders 48:149-55 (1998).
Freeman et al., "Randomized dose-ranging pilot trial of omega-3 fatty acids for postpartum depression", Acta Psychiatr. Scand. 113:31-35 (2006).
Grenyer et al., "Fish oil supplementation in the treatment of major depression: A randomised double-blind placebo-controlled trial", Progress in Neuro-Psychopharmacology and Biological Psychiatry 31:1393-96 (2007).
Hibbeln, "Seafood consumption, the DHA content of mothers' milk and prevalence rates of postpartum depression: a cross-national, ecological analysis", J. Affective Disorders 69:15-29 (2002).
Irmisch et al., "Relationships between fatty acids and psychophysiological parameters in depressive inpatients under experimentally induced stress", Prostaglandins, Leukotrienes and Essential Fatty Acids 74:149-56 (2006).
Irmisch et al., "Fatty acids and sleep in depressed inpatients", Prostaglandins, Leukotrienes and Essential Fatty Acids 76:1-7 (2007).
Kiecolt-Glaser et al., "Depressive Symptoms, omega-6:omega-3 Fatty Acids, and Inflammation in Older Adults", Psychosom. Med. 69:217-24 (2007).
Lin Et al., "A Meta-Analytic Review of Double-Blind, Placebo-Controlled Trials of Antidepressant Efficacy of Omega-3 Fatty Acids", J. Clin. Psychiatry 68(7):1056-61 (2007).
Logan, "Omega-3 fatty acids and major depression: A primer for the mental health professional", Lipids in Health and Disease 3:25 (2004).
Maes, et al., "Fatty acid composition in major depression: decreased omega-3 fractions in cholesteryl esters and increased C20: 4 omega-6/C20: 5 omega-3 ratio in cholesteryl esters and phospholipids", J. Affective Disorders 38:35-46 (1996).
Mamalakis et al., "Depression and adipose polyunsaturated fatty acids in an adolescent group", Prostaglandins, Leukotrienes and Essential Fatty Acids 71(5):289-94 (2004).
Mamalakis et al., "Depression and serum adiponectin and adipose omega-3 and omega-6 fatty acids in adolescents", Pharmacology, Biochemistry and Behavior 85:474-79 (2006).
Marangell et al., "A Double-Blind, Placebo-Controlled Study of the Omega-3 Fatty Acid Docosahexaenoic Acid in the Treatment of Major Depression", Am. J. Psychiatry 160(5):996-98 (2003).
Otto et al., "Increased risk of postpartum depressive symptoms is associated with slower normalization after pregnancy of the functional docosahexaenoic acid status", Prostaglandins, Leukotrienes and Essential Fatty Acids 69:237-43 (2003).
Parker et al., "Low levels of docosahexaenoic acid identified in acute coronary syndrome patients with depression", Psychiatry Research 141:279-86 (2006).
Peet et al., "A Dose-Ranging Study of the Effects of Ethyl-Eicosapentaenoate in Patients With Ongoing Depression Despite Apparently Adequate Treatment With Standard Drugs", Arch. Gen. Psychiatry 59:913-19 (2002).
Severus et al., "Omega-3 Fatty Acids—The Missing Link?", Arch. Gen. Psychiatry 56:380-81 (1999).
Tanskanen et al., "Fish Consumption and Depressive Symptoms in the General Population in Finland", Psychiatric Services 52(4):529-31 (2001).
Tiemeier et al., "Plasma fatty acid composition and depression are associated in the elderly: the Rotterdam Study", Am. J. Clin. Nutr. 78:40-6 (2003).
Van De Rest et al., "Effect of fish-oil supplementation on mental well-being in older subjects: a randomized, double-blind, placebo-controlled trial". Am. J. Clin. Nutr. 88:706-13 (2008).
Hodson et al., "Fatty Acid Composition of Adipose Tissue and Blood in Humans and Its Use As A Biomarker of Dietary Intake" Prog. Lipid Res. 47:348-80 (2008).

* cited by examiner

FATTY ACID PATTERN ANALYSIS FOR PREDICTING ACUTE CORONARY SYNDROME

CROSS REFERENCE

This application claims priority to U.S. Provisional Patent Application Ser. No. 61/135,822, filed Jul. 23, 2008, incorporated by reference herein in its entirety.

BACKGROUND OF THE INVENTION

Predicting risk for acute coronary syndromes (ACS) remains an inexact science. Although several recent risk prediction algorithms have been proposed, the original and most widely used system is from the Framingham Heart Study. The Framingham Risk Score (FRS) was designed to predict the 10-year risk for major coronary events, and it does so with a c-statistic [area under the receiver operating characteristic (ROC) curve] of 0.7-0.8. All of these prediction algorithms generally include age, sex, total (or low-density lipoprotein, LDL) cholesterol (C), high-density lipoprotein C (HDL-C), blood pressure and smoking and diabetic status when assigning risk. Despite the utility of the FRS in coronary heart disease (CHD) risk prediction, there remains a need for additional markers that improve upon this standard; while a number of putative risk factors have been tested, few have added meaningfully to the FRS.

SUMMARY OF THE INVENTION

In one aspect, the present invention provides methods for predicting the risk of acute coronary syndrome (ACS) in a human subject, comprising:
(a) measuring, in a fatty acid sample isolated from a blood component from a human subject, an amount of:
  (i) one or both of linoleic acid and gamma-linolenic acid; and
  (ii) one or both of docosahexaenoic acid (DHA) and eicosapentaenoic acid (EPA);
(b) comparing the amount of (a)(i) and (a)(ii) in the fatty acid sample to an amount of (a)(i) and (a)(ii) in a control; and
(c) predicting a risk of ACS based on the comparison.

In another aspect, the present invention provides methods for predicting the risk of acute coronary syndrome (ACS) in a human subject, comprising:
(a) measuring, in a fatty acid sample isolated from a blood component from a subject, an amount of:
  (i) at least two of linoleic acid, gamma-linolenic acid, oleic acid, palmitic acid, and alpha-linolenic acid; and
  (ii) one or more of docosatetraenoic acid, docosahexaenoic acid (DHA), trans-oleic acid, n-3 docosapentaenoic acid, eicosapentaenoic acid (EPA), n-6 docosapentaenoic acid, arachadonic acid, linoleic acid, gamma-linolenic acid, oleic acid, stearic acid, and alpha-linolenic acid,
  wherein there is no overlap between fatty acids in (a)(i) and (a)(ii)
(b) comparing the amount of (a)(i) and (a)(ii) in the fatty acid sample to an amount of (a)(i) and (a)(ii) in a control; and
(c) predicting a risk of ACS based on the comparison.

Various preferred embodiments of each aspect are described in detail below. In one such embodiment, comparing the amount of the one or more fatty acids to a control comprises multiplying the percent total of the relevant fatty acids by a predetermined risk factor coefficient to produce an individual fatty acid score and summing the individual fatty acid scores to produce a risk score.

In another preferred embodiment of each aspect, the method further comprises subjecting the percent total of the relevant fatty acids in the fatty acid sample to an analysis selected from the group consisting of generalized models, multivariate analysis, and time-to-event survival analysis, to produce a modified risk score; wherein the modified risk score is used to correlate with ACS in the human subject.

In a further preferred embodiment of each aspect, the method further comprises determining a Framingham risk score for the subject.

In a further aspect, the present invention provides physical computer readable storage media comprising a set of instructions for causing a device for measuring fatty acids in a fatty acid sample to carry out the methods of any of the aspects and embodiment of the invention.

BRIEF SUMMARY OF THE FIGURES

FIG. 1 depicts a flowchart describing recruitment of study subjects. Cases were drawn from a prospective registry of patients with a confirmed diagnosis of ACS (2187). Patients that were excluded from the study (526) include those refused interview/access (128), discharged or transferred prior to interview (308), deceased (27), and other categories (63) including hard of hearing, too ill for interview, dementia, not English speaker and weekend admission. Among the total of enrolled 1,661 patients, 1059 samples were obtained. No samples were obtained for 602 patients, including those who refused extra venipuncture, had insufficient blood volume left over, were discharged prior to interview, and refused to allow use of blood for biomarker testing. Moreover, patients were also excluded (represented by "No data (100)") due to incomplete information on some of the standard coronary heart disease (CHD) risk factors including HDL(98), total cholesterol (89) and smoking status (2). Similarly, outpatient controls were also excluded (represented by "No data (88)") due to incomplete information on some of the standard coronary heart disease (CHD) risk factors including HDL(1), total cholesterol (1), hypertension (28), diabetes mellitus (58), age (1) and smoking status (19).

FIG. 2 is a graph demonstrating discrimination between ACS cases and controls in the validation set (n=450) with receiver operating characteristic curves. Areas under the curves (c-statistics) were compared for the modified Framingham risk score alone (c=0.77; broken gray line), the blood cell FA model alone (c=0.85; solid black line), and the FA plus modified Framingham model (c=0.88; dashed black line). C-statistics for both models including FAs were significantly greater than the Framingham model but were not different from each other (Table 3; abbreviations as in Table 1). The diagonal line represents "Chance," also known as "line of no-discrimination," which is a random-guess line, showing that the percentage of being true or false is 50% for any points on this line.

DETAILED DESCRIPTION OF THE INVENTION

In a first aspect, the present invention provides methods for predicting the risk of ACS in a human subject, comprising:
(a) measuring, in a fatty acid sample isolated from a blood component from a human subject, an amount of:
  (i) one or both of linoleic acid and gamma-linolenic acid; and
  (ii) one or both of docosahexaenoic acid (DHA) and eicosapentaenoic acid (EPA);

(b) comparing the amount of (a)(i) and (a)(ii) in the fatty acid sample to an amount of (a)(i) and (a)(ii) in a control; and (c) predicting a risk of ACS based on the comparison.

As disclosed in detail below, the inventors have discovered that specific fatty acid pattern in a fatty acid sample isolated from blood component can be used in the diagnosis and prognosis of ACS. Such fatty acid (FA) profiles are unexpectedly demonstrated to add substantially to ACS case discrimination based on the state of art techniques such as the Framingham Risk Score. Even more surprisingly, the inventors have discovered that certain FA profiles alone are able to discriminate ACS cases from controls better than the Framingham Risk Score model. Thus, without knowledge of serum lipid levels, hypertensive and smoking status, personal/family histories of coronary heart disease (CHD), or diabetes status, the methods of the present invention alone can be used to predict ACS case status with a relatively high degree of accuracy, and thus may improve identification of patients at increased risk for ACS, which can lead to earlier and more aggressive treatment.

As used herein, acute coronary syndrome (ACS) covers any group of clinical symptoms compatible with acute myocardial ischemia (see American Heart Association web site, americanheart.org/presenter.jhtml?identifier=3010002). Acute myocardial ischemia is chest pain due to insufficient blood supply to the heart muscle that results from coronary artery disease, and includes myocardial infarction and unstable angina.

ACS is usually associated with coronary thrombosis, but can also be associated with cocaine use. Symptoms associated with ACS include, but are not limited to, chest pain, chest tightness, anemia, bradycardia, tachycardia, and heart palpitations. Thus, subjects presenting with one or more of these symptoms will benefit from the methods of the invention, as well as those subjects that have a family history of ACS or symptoms thereof, a genetic predisposition to ACS, other risk factors for ACS, and/or have previously suffered from ACS.

The methods of the invention can be used alone or in combination with other methods for diagnosing risk of and/or presence of ACS, including but not limited to electrocardiograms, blood tests for ACS biomarkers (including but not limited to creatine kinase MB, troponin I, troponin T, and natriuretic peptide), chest X-rays, and Framingham Risk Score analysis, discussed in detail in the examples below.

As used herein, a "blood component" is whole blood or any specific fraction thereof. In various embodiments, the blood component is selected from the group consisting of red blood cells, whole blood, serum/plasma, platelets, white blood cells, and serum/plasma lipid classes such as phospholipids, cholesteryl esters, triglycerides or free fatty acids. As noted below, blood component can be used for isolation of the fatty acid sample immediately upon obtaining the blood component, or it can be frozen and thawed prior to use. Fatty acids are isolated from the blood component (to generate the "fatty acid sample") using standard methods known to those of skill in the art, which comprises either isolation immediately before carrying out the methods, or isolation and subsequent storage (on ice, frozen, etc.) of the fatty acid sample. In a preferred embodiment, the fatty acid sample is isolated from blood cell membranes, such as red blood cells, platelets, or white blood cells. In preferred embodiments, the fatty acid sample includes all of the fatty acids from the blood component, such as the entire fatty acid complement isolated from blood cell membranes. Exemplary methods for preparation of fatty acids from such blood components can be found in Block et al., Atherosclerosis 2008 April; 197(2):821-8, and exemplary such methods are disclosed herein. As will be understood by those of skill in the art, the fatty acid sample may contain components other than fatty acids; the sample is "isolated" in the sense that it is removed from its natural environment in the blood component, such as being removed from blood component membranes.

Determining an amount of the fatty acids can comprise any suitable measurement, including but not limited to determining an amount of a fatty acid for the blood component as a weight percentage of total fatty acids, a molar percentage of total fatty acids, a concentration in the blood component, etc.

As used herein, a "control" is any means for normalizing the amount of the one or more fatty acids (FA) being measured from the human subject to that of a standard. In one embodiment, the control comprises pre-defined fatty acid levels from a normal individual or population (ie: known not to be suffering from ACS), or from an individual or population of subjects suffering ACS. In another embodiment, the control comprises a known amount of the one or more FA from the blood component being sampled in ACS or non-ACS subjects. In these embodiments, predicting a risk of ACS in the subject based on the measuring may comprise detecting a similar pattern of the fatty acid markers in the subject as in a control subjects with ACS or in a control subject that later progressed to ACS, or may comprise detecting a dissimilar pattern from control subjects known not to have had ACS.

In another embodiment, the comparison may comprise adjusting the amount of the fatty acids by an appropriate weighting coefficient, hereinafter referred to as "a beta coefficient." In one embodiment, the method comprises (a) multiplying the amount of the fatty acids (expressed as a percentage of total fatty acids in the sample) by a predetermined beta coefficient to produce an individual fatty acid score; and (b) summing the individual fatty acid scores to produce a risk score. This risk score can then be used in another equation to determine the probability that a given subject has ACS or is at higher risk for developing ACS than a person with a lower score. As will be understood by those of skill in the art based on the teachings herein, beta coefficients can be determined by a variety of techniques and can vary widely. In one example of determining appropriate beta coefficients, multivariable logistic regression (MLR) is performed using the fatty acids values found within two groups of patients, for example, one with and one without ACS. There are several methods for variable (fatty acids) selection that can be used with MLR, whereby the fatty acids not selected are eliminated from the model and the beta coefficients for each predictive fatty acid remaining in the model are determined. These beta coefficients are then multiplied by the fatty acid content of the sample (expressed as a percentage of total fatty acids in the sample) and then summed to calculate a weighted score. The resulting score ("the risk score") can then be compared with a particular cutoff score (ie: a threshold), above which a subject is diagnosed as at increased risk for suffering from ACS or not at increased risk for suffering from ACS.

In various further embodiments, the fatty acid data (including, but not limited to, percentage total of the individual one or more fatty acids, molar percentage of total fatty acids in the blood component, a concentration in the blood component, etc.) are subjected to one or more alternative transformative analyses, including but not limited to generalized models (e.g. logistic regression, generalized additive models), multivariate analysis (e.g. discriminant analysis, principal components analysis, factor analysis), and time-to-event "survival" analysis to produce a modified score; wherein the modified score can be used to determine a risk for ACS.

In exemplary embodiments of the methods, Multivariable Logistic Regression (MLR) or Discriminant Analysis (DA)

can be used as classification methods for determining the probability of ACS. Fatty acids are assumed to be independent in MLR and to be inter-correlated in DA. The fatty acids are the predictor variables ($X_i$'s) and the probability for ACS is the outcome (Y). The probability is a continuous variable which can be dichotomized into two levels such as a binomial (0=Low risk or No Disease, 1=High Risk or Disease) response or several discrete levels as an ordinal response (0, 1, 2, etc. for different risk levels for ACS).

The inventors have discovered that the amount of linoleic acid, gamma-linolenic acid, DHA, and EPA in isolated blood component fatty acid samples are each inversely correlated with the risk of ACS in the human subject. As used herein, "inversely correlated" means that a higher amount of fatty acid relative to a control means the subject is at lower risk to have ACS, while "directly correlated" means a higher amount of the fatty acid relative to a control means the subject is more likely to have ACS.

In this first aspect, any combination of (i) one or both of linoleic acid and gamma-linolenic acid; and (ii) one or both of docosahexaenoic acid (DHA) and eicosapentaenoic acid (EPA) can be used. In one embodiment of this first aspect, the measuring comprises measuring an amount of linoleic acid and one or both of DHA and EPA in the fatty acid sample. In another embodiment, the measuring comprises measuring an amount of linoleic acid, DHA, and EPA in the fatty acid sample. In a further embodiment, the measuring comprises measuring an amount of gamma-linolenic acid and one or both of DHA and EPA in the fatty acid sample. In a still further embodiment, the measuring comprises measuring an amount of gamma-linolenic acid, DHA, and EPA in the fatty acid sample. As detailed in the examples that follow, the inventors have demonstrated that the methods of each of these embodiments can be used to diagnose ACS as a stand alone method, or in combination with other techniques, such as Framingham Risk Score (FRS) analysis and/or use of one or more of the FRS predictor variables (Sex, Age, Hypertension, Diabetes Mellitus, Current Smoker, Total-Chol, HDL-Chol) in a composite model with the fatty acids disclosed herein.

In another embodiment of this first aspect of the invention, the method further comprises (d) measuring an amount of one or more fatty acids selected from the group consisting of alpha-linoleic acid, palmitic acid, stearic acid, trans-oleic acid, n-6 docosapentaenoic acid, docosatetraenoic acid, arachidonic acid, oleic acid, n-3 docosapentaenoic acid, palmitoleic acid, trans-palmitoleic acid, and eicosadienoic acid in the fatty acid sample;

(e) comparing the amount of the one or more fatty acids selected from the group to an amount of the one or more fatty acids selected from the group in the control; and (f) using the comparison in step (e) in predicting the risk of ACS.

These embodiments can be used to improve ACS risk prediction over that provided by the FA combinations recited above.

The inventors have discovered that the amount of alpha-linolenic acid, palmitic acid, stearic acid, n-6 docosapentaenoic acid, docosatetraenoic acid, arachidonic acid, oleic acid, n-3 docosapentaenoic acid, palmitoleic acid in an isolated blood component fatty acid sample are inversely correlated with the risk of ACS in a human subject, and the amount of trans oleic acid and eicosadienoic acid in the isolated fatty acid sample are directly correlated with the risk of ACS in the human subject. This embodiment may comprise measuring the amount of 1, 2, 3, 4, 5, 6, 7, 8, 9, 10, 11 or all 12 of the fatty acids recited in (d) in comparison to control.

In another preferred embodiment of the methods of this first aspect of the invention, the measuring comprises measuring an amount of linoleic acid, DHA, and EPA in the fatty acid sample, and further comprises (d) measuring an amount of each fatty acid selected from the group consisting of stearic acid, alpha-linoleic acid, gamma-linolenic acid, palmitoleic acid, arachadonic acid, trans-palmitoleic acid, eicosadienoic acid, and trans-oleic acid in the fatty acid sample;

(e) comparing the amount of each fatty acid measured in step (d) to an amount of each fatty acid selected from the group in the control; and (f) using the comparison in step (e) in predicting the risk of ACS.

This embodiment is detailed in Example 1 below; see, for example, Table 2. This embodiment may comprise measuring the amount of 1, 2, 3, 4, 5, 6, 7, or all 8 of the fatty acids recited in step (d) in comparison to control.

In a further preferred embodiment of this first aspect of the invention, the measuring comprises measuring an amount of linoleic acid and one or both of DHA and EPA in the fatty acid sample, and further comprises (d) measuring an amount of one or more fatty acids selected from the group consisting of gamma-linolenic acid, alpha-linolenic acid, palmitic acid, stearic acid, trans-oleic acid, n-6 docosapentaenoic acid, docosatetraenoic acid, arachidonic acid, oleic acid, n-3 docosapentaenoic acid, palmitoleic acid, trans palmitoleic, and eicosadienoic acid in the fatty acid sample;

(e) comparing the amount the one or more fatty acids measured in step (d) to an amount of the one or more fatty acids in the control; and (f) using the comparison in step (e) in predicting the risk of ACS.

This embodiment is detailed in Example 2 below; for example, see Table 4. This embodiment may comprise measuring the amount of 1, 2, 3, 4, 5, 6, 7, 8, 9, 10, 11, 12 or all 13 of the fatty acids recited in step (d) in comparison to control.

In a further preferred embodiment of this first aspect of the invention, the measuring comprises measuring an amount of gamma-linolenic acid and one or both of DHA and EPA in the fatty acid sample, and the method further comprises (d) measuring an amount of one or more fatty acids selected from the group consisting of palmitic acid, alpha-linolenic acid, oleic acid and palmitoleic acid in the fatty acid sample; and (e) comparing the amount the one or more fatty acids measured in step (d) to an amount of the one or more fatty acids in the control; and (f) using the comparison in step (e) in predicting the risk of ACS.

This embodiment is detailed in Example 2 below; for example, see Table 4. This embodiment may comprise measuring the amount of 1, 2, 3, or all 4 of the fatty acids recited in step (d) in comparison to control.

In a second aspect, the present invention provides methods for predicting the risk of acute coronary syndrome (ACS) in a human subject, comprising:

(a) measuring, in a fatty acid sample isolated from a blood component from a subject, an amount of:
   (i) at least two of linoleic acid, gamma-linolenic acid, oleic acid, palmitic acid, and alpha-linolenic acid; and
   (ii) one or more of docosatetraenoic acid, trans-oleic acid, n-3 docosapentaenoic acid, docosahexaenoic acid (DHA), eicosapentaenoic acid (EPA), n-6 docosapentaenoic acid, arachadonic acid, linoleic acid, gamma-linolenic acid, oleic acid, stearic acid, and alpha-linolenic acid, wherein there is no overlap between fatty acids in (a)(i) and (a)(ii);

(b) comparing the amount of (a)(i) and (a)(ii) in the fatty acid sample to an amount of (a)(i) and (a)(ii) in a control; and (c) predicting a risk of ACS based on the comparison.

All definitions and embodiments disclosed in the first aspect of the invention are equally applicable in this second embodiment, unless the context clearly dictates otherwise. This aspect of the invention provides further methods for diagnosing ACS, and numerous examples are provided in Example 2 below (see, for example, see Table 4), and can be used as a stand alone method, or in combination with other techniques, such as Framingham Risk Score analysis. This embodiment may comprise measuring the amount of any combination of the (a)(i) and (a)(ii) fatty acids in comparison to control.

As recited in this aspect, the recitation that there is "no overlap between fatty acids in (a)(i) and (a)(ii)" means that the same fatty acid cannot satisfy the fatty acid requirement for both (a)(i) and (a)(ii). For example, if the (a)(i) fatty acids include linoleic acid and gamma-linolenic acid, then the (a)(ii) fatty acid must be something other than linoleic acid or gamma-linolenic acid.

In one preferred embodiment of this second aspect, the (a)(i) fatty acids comprise linoleic acid and gamma-linolenic acid, and the (a)(ii) fatty acids comprise one or more fatty acids selected from the group consisting of oleic acid, n-3 docosapentaenoic acid, stearic acid, and palmitic acid. This embodiment may comprise measuring the amount of 1, 2, 3, or all 4 of the (a)(ii) fatty acids in comparison to control.

In a further preferred embodiment of this second aspect, the (a)(i) fatty acids comprise gamma-linolenic acid and oleic acid, and the (a)(ii) fatty acids comprise one or more fatty acids selected from the group consisting of alpha-linolenic acid, docosatetraenoic acid, n-6 docosapentaenoic acid, and arachidonic acid. This embodiment may comprise measuring the amount of 1, 2, 3, or all 4 of the (a)(ii) fatty acids in comparison to control.

In another preferred embodiment of this second aspect, the (a)(i) fatty acids comprise palmitic acid and alpha-linolenic acid, and the (a)(ii) fatty acids comprise one or more fatty acids selected from the group consisting of trans-oleic acid, eicosapentaenoic acid (EPA), gamma-linolenic acid, docosatetraenoic acid, and linoleic acid. This embodiment may comprise measuring the amount of 1, 2, 3, 4 or all 5 of the (a)(ii) fatty acids in comparison to control.

In yet another preferred embodiment of this second aspect, the (a)(i) fatty acids comprise linoleic acid and alpha-linolenic acid, and the (a)(ii) fatty acids comprise one or more fatty acids selected from the group consisting of oleic acid and n-3 docosapentaenoic acid. This embodiment may comprise measuring the amount of 1 or both of the (a)(ii) fatty acids in comparison to control.

In a still further preferred embodiment of this second aspect, the (a)(i) fatty acids comprise palmitic acid and docosatetraenoic acid, and the (a)(ii) fatty acids comprise gamma-linolenic acid.

In another preferred embodiment of this second aspect, the (a)(i) fatty acids comprise palmitic acid and trans-oleic acid, and the (a)(ii) fatty acids comprise linoleic acid.

Each of these preferred embodiments of the second aspect of the invention are disclosed in more detail below in Example 2. Any of these embodiments of the second aspect of the invention may further comprise measuring the amount of one or more further fatty acids to help further improve statistical significance of FA marker performance in diagnosing ACS. Such additional fatty acids may include any of those disclosed herein in either aspect of the invention that are not already recited in the relevant embodiment.

In any embodiment of the first or second aspect of the invention, the fatty acid samples may be treated to produce fatty acid methyl esters (FAMES) prior to measuring the amount of the relevant fatty acids in the fatty acid sample. In one preferred embodiment, methylation comprises treatment of the fatty acid sample with a boron-trifluoride solution, preferably at elevated temperature (90° C. or more; more preferably approximately 100° C.). The method may then further comprise extracting FAMEs from the tissue sample using a hexane solvent, and may further comprise separating the FAMEs by gas chromatography and determining retention times of the FAMEs in the column by any suitable means, such as use of a flame ionization detector (FID). Such retention times can be compared to a FAME standard and used in the FA measuring and comparing steps recited herein. In one embodiment, the methods may comprise subjecting the blood component to one or more freeze-thaw cycles prior to production of FAMES; this embodiment is of particular value when the blood component is frozen. Any suitable number of freeze-thaw cycles can be used; it is within the level of skill in the art to determine specific freeze-thaw conditions for a given analysis. Similarly, it is within the level of skill in the art, based on the teachings herein, to determine suitable methylation conditions, gas chromatography conditions, and FID conditions for a given assay. Exemplary conditions are provided below.

In one embodiment, the measuring step comprises calculating a FAME response factors for each FAME. Such calculations may be done by any suitable method. In one embodiment, determining a FAME response factor comprises:

(i) identifying the area counts for a reference fatty acid in the FAME standard and dividing the area counts by the known area percent of the reference fatty acid in the FAME standard; this establishes a certain number of area counts per percent composition in the FAME standard (hereafter the reference ratio)

(ii) multiplying the known percent composition of all other fatty acids in the FAME standard by the reference ratio to generate adjusted area counts (iii) dividing the observed area counts for each fatty acid in the FAME standard by the adjusted area counts to generate a response factor;

(iv) multiplying the observed area counts for each fatty acid in a sample by its own response factor to produce adjusted area counts for each fatty acid in the sample; and (v) summing all of the adjusted area counts for all of the fatty acids in the sample and then dividing the adjusted area counts for each individual fatty acid by the total adjusted area counts in order to express each fatty acid in the sample as a percent of total fatty acids in the sample.

In one example of this embodiment, assume that the area counts for a reference FA in the FAME standard (such as C16:0, palmitic acid) are found to be 1000, and the known percent composition of palmitic acid in the FAME standard is 10% of total fatty acids. The area counts are divided by the percent composition (1000/10) to give a value of 100 area counts per 1 percent of fatty acids. This value is then applied to all other fatty acids in the FAME standard. For example, if the known percent composition of oleic acid is 20% in the FAME standard then the expected area counts for oleic acid should be 20×100, or 2000 area counts. However, say the observed area counts for oleic acid are 1900 counts. This is artificially low and may be adjusted upwards. Accordingly, the observed area counts are divided by the expected area counts (1900/2000=0.95) to generate a response factor for oleic acid, here 0.95. This is done for all fatty acids in the FAME standard. The response factors thus determined are then applied to the observed fatty acid area counts in the unknown samples. For example, assume that a hypothetical sample contained only 3 fatty acids (impossible in vivo, but illustrative). Assume that the area counts of oleic acid, linoleic acid and stearic acid in the unknown were 100, 200 and 400 counts, respectively, for a total of 700 area counts. Without adjustment for response factors, the percent composition would be 14%, 28% and 56%. Assume however, that the response factors (as determined from running the FAME standard in the same batch) were 0.90, 1.05 and 0.98, respectively. Adjusting the observed area counts by the response factors would give 90, 210, and 392 adjusted area counts. Summing these three=692 total adjusted area counts. The percent compositions based on the adjusted area counts then become 13%, 30% and 57%.

Note that any of the foregoing embodiments of any aspect may be combined together to practice the claimed invention, unless the context clearly dictates otherwise.

In a further aspect, the present invention provides physical computer readable storage media, for automatically carrying out the methods of the invention on a computer linked to a device for measuring fatty acids in a fatty acid sample, such as those disclosed herein. As used herein the term "computer readable medium" includes magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system.

Example 1

We disclose a metabolomic approach based on blood cell fatty acid (FA) profiles in fatty acid samples isolated from blood cell components that can discriminate acute coronary syndrome (ACS) cases from controls, and have discovered that analysis of such FA profiles can improve discrimination of ACS compared with established risk factors. Multivariable logistic regression models based on FA profiles ($MLR_{FA}$) and a modified Framingham risk score ($MLR_{FR}$s) were developed on a random $\frac{2}{3}^{rd}$ training set and tested on a $\frac{1}{3}^{rd}$ validation set. The area under receiver operating characteristic (ROC) curves (c-statistics), misclassification rates, and model calibrations were used to evaluate the individual and combined models. The $MLR_{FA}$ discriminated cases from controls better than the MLRFRs (c=0.85 vs. 0.77, p=0.003) and the FA profile added significantly to the FRS model (c=0.88 vs. 0.77, p<0.0001). Hosmer-Lemeshow calibration was poor for the $MLR_{FA}$ model alone (p=0.01), but acceptable for both the $MLR_{FR}$s (p=0.30) and combined models (p=0.22). Misclassification rates were 29%, 23% and 20% for $MLR_{FR}$s, the $MLR_{FA}$, and the combined models, respectively. FA profiles contribute significantly to the discrimination of ACS cases, especially when combined with the modified FRS.

Methods

Figure 1:
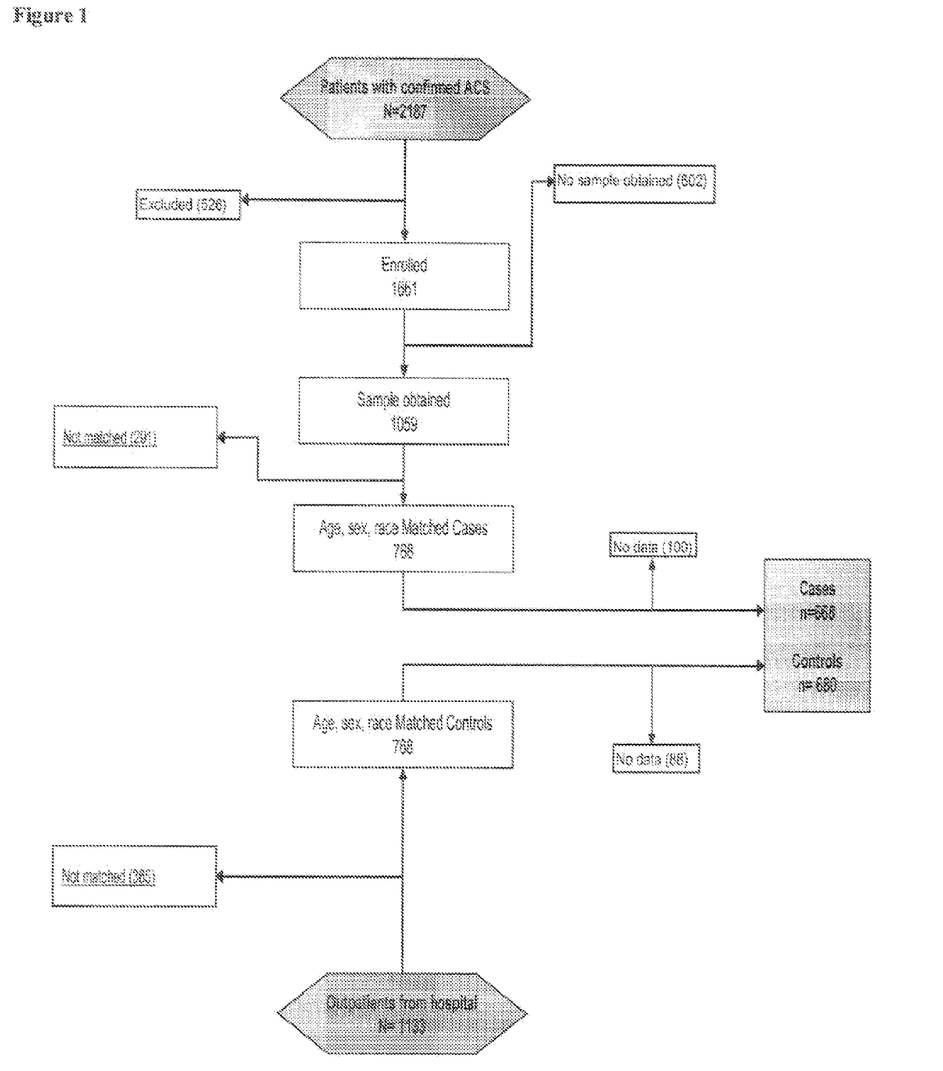

Selection of Cases. Cases were drawn from a prospective registry of patients with a confirmed diagnosis of either acute myocardial infarction[22] or unstable angina[23] as previously described[24] and as outlined in FIG. 1. All consecutive patients admitted to two hospitals associated with the University of Missouri-Kansas City School of Medicine were prospectively screened for an ACS between March 2001 and June 2004. Patients presenting with suggestive cardiac symptoms and/or ischemic ECG changes, and a positive troponin blood test, were considered to have had an MI. Patients were classified as having unstable angina if they presented with a negative troponin test, new onset angina (<2 months) of at least Canadian Cardiovascular Society Classification class III, prolonged (>20 minutes) rest angina, recent (<2 months) worsening of angina, or angina that occurred within 2 weeks of a previous MI. Although EKG changes were not a requirement for a diagnosis of unstable angina, over two-thirds had ischemic EKG changes on admission. To further increase the accuracy of the unstable angina diagnosis, those patients with a subsequent diagnostic study that excluded symptomatic ischemic heart disease (e.g. coronary angiography, nuclear or echocardiographic stress testing) or confirmed an alternative explanation for their presentation (e.g., esophagogastroduodenoscopy) were excluded. Three physicians reviewed the charts of all patients for whom diagnostic uncertainty remained and attained consensus on the final diagnosis. With this approach, a total of 1,661 patients were included in this registry and enrolled as described in FIG. 1.

Selection of Controls: Outpatient controls having blood drawn for routine clinical testing were recruited from blood drawing centers at Saint Luke's Hospital (where 88% of the cases were derived) between March 2004 to March 2005 as outlined in FIG. 1. By selecting controls from an outpatient clinical laboratory, we were able to include patients with medical issues warranting care, but not being treated for an ACS. Patients entering the centers were passively invited (by a sign placed on the registration desk) to participate in the study by completing a 2-page questionnaire and then allowing the phlebotomist to collect one additional 10 mL blood sample. Participation was limited to men and non-pregnant women age 35 and older. From the pool of control samples collected, cases were matched by age (5-yr windows), sex, and race (Caucasian vs. non-Caucasian for analysis) FIG. 1. A history of CHD was not an exclusion for either cases or controls, congruent with the intent of the study to identify patients at elevated risk for ACS, rather than CAD. The study was approved by the Institutional Review Boards of both hospitals.

Laboratory Methods: Blood cell FA composition was measured as previously described in detail[10] during the same time period regardless of sample date. As only frozen whole blood was available for this analysis, steps were taken to isolate blood cell membranes from serum lipoproteins. This was accomplished by placing 0.25 mL of thawed whole blood into a 1.75 mL of distilled water (to further assure erythrocyte lysis) and centrifuging at 4° C. for 5 min. at 10,000 rpm in a TLA100.3 rotor in a TL100 tabletop ultracentrifuge (Beckman Instruments, Fullerton, Calif.). The supernatant containing plasma lipids and hemoglobin was decanted, the membrane pellet was resuspended in methanol containing 14% boron trifluoride and transferred to a screw cap test tube. This was heated at 100° C. for 10 mm to generate FA methyl esters from the membrane glycerophospholipids. Equal portions of hexane and water were added to extract the methyl esters which were subsequently analyzed by flame ionization gas chromatography (GC). GC analysis was carried out with an Agilent 6890 (Agilent Technologies, Palo Alto, Calif.) equipped with a capillary column (SP2560, 100 m., Supelco, Bellefonte, Pa.). A custom-made mixture of FA (designed to mimic erythrocyte FA composition; GLC 673b, Nuchek Prep, Elysian, Minn.) was included as an external standard with each run for peak identification and for response factor adjustment. The response factor for palmitic acid was assumed to be 1.0, and that for all other FA was calculated based on this reference. FA peak areas were adjusted on a daily basis using these response factors, and reported as a percent of the total area for identified peaks. Each peak selected by the software algorithm was reviewed by a clinical chemist (who had an M.S. degree, 20 years of clinical laboratory experience, and was blinded to case status). In situations where the software identified peaks erroneously or failed to draw appropriate baselines, these errors were manually corrected and the chromatogram re-integrated. Matched case-control sample pairs were always analyzed in the same batch (20-30 samples), and were analyzed in random order along with standards and two controls (red blood cells high and low in omega-3 FAs). About 50 samples initially produced unacceptable chromatograms. Upon re-analysis, all samples generated acceptable data. During the 8-month analytic period, the Coefficient of Variation (CV) for high abundance FAs (>5.0%) was between 0.3% and 1.0%, and for low abundance FAs (<1.5%) it was between 1.6% and 5.8%. The minimum detection level of the equipment was 0.01%.

For the cases, serum lipids were measured in the hospital laboratory by routine enzymatic methods as clinically indicated within 1-2 days of admission. Lipid levels in control samples were determined in frozen plasma samples all at once at the end of the study using a Cobas Mira (Roche Diagnostics) in the Lipid Research Laboratory at Saint Luke's Hospital, a laboratory participating in the Lipid Standardization Program from the NHLBI/CDC. Appropriate corrections for differences in clinical lab and research lab lipid analyses were applied after a preliminary cross-lab comparison.

Statistical Methods: The original dataset contained 768 patients diagnosed with acute coronary syndrome (ACS) which were matched one-to-one with controls on the basis of age, gender, and race. The 1,576 patients were reduced to 1,348 due to incomplete information on some of the standard coronary heart disease (CHD) risk factors including: HDL, total cholesterol, self-reported hypertension (HTN), self-reported diabetes mellitus (DM), age, gender, and current smoking status shown in FIG. 1. If there were zeros present for any of the 18 FAs then the smallest non-zero value was used as the minimum detection level and the zeros were replaced by ½ of the minimum detection level. Two-thirds of the 1,348 subjects were randomly selected (without regard to matching or case status) as a training dataset for model building, while the remaining one-third was used later as a validation dataset to estimate prediction capabilities. The training and validation datasets contained 445 and 223 cases, and 453 and 227 controls, respectively. The statistical models described below were analyzed by solely including the FAs, and additionally by adding the FAs to the 7 traditional CHD risk factors comprising the FRS. Since the FRS is intended for risk prediction only in untreated subjects, we did a subgroup analysis including only those individuals who were not taking statin drugs.

Statistical Models

Modified Framingham Risk Score (FRS)—The FRS includes seven factors: age, sex, total (or LDL) C, HDL-C, systolic and diastolic blood pressure, diabetes (based on blood glucose) and smoking status. Since for the controls, we did not have independent evidence of diabetic status or specific systolic and diastolic values, we included self-reported diabetes and hypertension as dichotomous variables along with the other five factors in a multivariable logistic regression ($MLR_{FRS}$) model (the modified FRS). Natural log transformations were used for HDL and total cholesterol to improve normality.

Fatty, Acid-Based Metabolomics—A model was developed ($MLR_{FA}$) using stepwise selection to reduce the number of fatty acids to a subset of the most significant in collectively predicting case status; a p-value of 0.01 was used to enter and remain in the model considering the multiple predictor variables. A third MLR model$_{(MLRFRs+FA)}$ was developed including the FAs selected in the $MLR_{FA}$ combined with the traditional CHD risk factors used in the $MLR_{FRS}$. Robust, non-parametric 95% confidence intervals (CI) of the parameter estimates were obtained using bootstrapping method with 10,000 replicates from the training data set for both FA models. In addition to using the stepwise selected FAs, four pre-specified FA metrics were also tested for their ability to add to the FRS model: the omega-3 index (EPA+DHA)[25], the n-6:n-3 ratio[26], the total long-chain n-3 FAs (EPA+DHA+DPA), and the proportion of the long-chain n-3 plus n-6 FAs that were of the n-3 family[27].

For each MLR model, a single continuous variable, a risk score, was calculated (equation 1) as the linear combination of the parameter estimates ($\beta_i$, i=0 to p) multiplied by each subject's FA levels (expressed as a percent of total FAs) or the traditional risk factors for the FRS ($x_{ij}$, j=1 to n) as follows:

$$riskscore=\beta_0+\beta_1 x_{1j}+\beta_2 x_{2j}\ldots+\beta_p x_{pn} \quad \text{Equation 1}$$

The risk score was then used to determine (equation 2) the probability of case status, Pr(case). A Pr(case)>0.5 (the cut-point threshold) was classified as a case, otherwise as a control.

$$Pr(case)=1/(1+e^{-(riskscore)}) \quad \text{Equation 2}$$

Performance Metrics

Several metrics were examined to compare the performance of the various models using the validation set.[16-20] Discrimination was assessed with the c-statistic (concordance index) which summarizes the continuum of model sensitivity and specificity values into a single measure. Positive likelihood ratios combine in one number the sensitivity and specificity at the cut-point threshold by dividing the proportion of true positives by the proportion of false positives. This statistic indicates how likely it is that a case will have an abnormal test compared to a control, given 2 random patients, one of whom is a case and the other a control. Calibration was examined using the Hosmer-Lemeshow statistic, a goodness-of-fit measurement that compares predicted to observed counts of subjects by risk score deciles. Misclassification rates were also determined.

The area under the ROC curve (c-statistic) was determined and the difference compared to the $MLR_{FRS}$ was tested. To account for multiple testing, the Dunnett adjustment was made to the 95% confidence intervals (CI). The standard error (SE) for the c-statistic was computed as described by Hanley and McNeil[28] taking into account the fact that the areas were correlated since the same patient data were used in each method[29].

Results

Case-control differences: Due to prospective matching on age, sex and race, there were no differences in these attributes (Table 1). As expected, classic CHD risk factors were generally more common among cases than controls. Twelve of the 18 FAs differed between groups, with cases having lower levels in 6 and higher levels in the other 6 FAs (Table 1).

Parameter estimates: Stepwise selection identified ten FAs significantly related to ACS case status comprising the final model (Table 2).

Two FAs (eicosadienoic acid and trans oleic acid) were directly related to case status, whereas the other eight were inversely related. On a per-standard deviation basis, the greatest contributor to case status prediction among the latter was linoleic acid, followed by stearic acid, DHA and the others.

Figure 2:
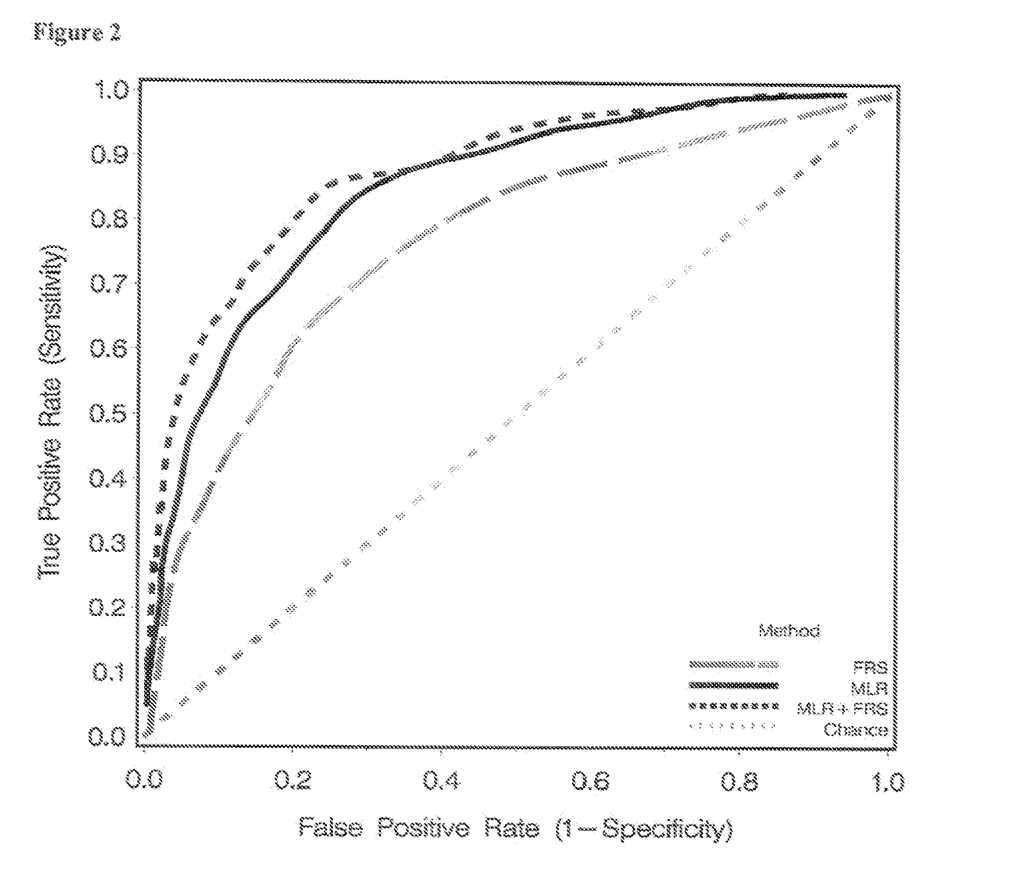

Model Discrimination: Using the standard risk factors, and the parameter estimates for blood cell FAs, the ability of MLR models to discriminate cases from controls were compared, both alone and in combination (Table 3 and FIG. 2).

The $MLR_{FA}$ performed better than the $MLR_{FRS}$, with a c-statistic 8 percentage points higher (p=0.003). Adding the FA profile to the FRS significantly increased the c-statistic of the latter by 11 percentage points (p<0.0001), whereas the FA-profile derived c-statistic was not significantly improved by including the standard risk factors (0.85 to 0.88, p=0.16). Although the 10-FA profile added significantly to the FRS model, none of the simpler, pre-defined FA metrics (e.g., the omega-3 index, the Lands' index, the n6:-3 ratio, etc.) added significantly to $MLR_{FRS}$ discrimination (data not shown). As expected, in the statin-nayve subgroup, the $MLR_{FRS}$ c-statistic was significantly improved over that in the group as a whole (0.81 vs 0.77, p=0.0002), but the addition of the FA profile still added significantly to the c-statistic (0.89 vs 0.81, p=0.002) even in this subgroup.

TABLE 1

Baseline Characteristics of Cases and Controls (N = 1,348)

| Variable | Cases (n = 668) | Controls (n = 680) | P-value* |
|---|---|---|---|
| Demographics | | | |
| Caucasian | 611 (91)† | 624 (92) | 0.84 |
| Body mass index [kg/m²] | 29 (25, 33)‡ | 27 (25, 31) | <0.0001 |
| Myocardial infarction or revascularization (by history) | 567 (85) | 141 (21) | <0.0001 |
| Family history of premature CHD | 356 (53) | 239 (36) | <0.0001 |
| Statin use | 290 (43) | 258 (38) | 0.04 |
| Standard CVD Risk Factors | | | |
| Age [yr] | 59 (52, 70) | 59 (52, 70) | 0.94 |
| Male | 445 (67) | 448 (66) | 0.78 |
| Hypertension (by history) | 423 (63) | 361 (53) | 0.0001 |
| Total cholesterol [mg/dL] | 176 (148, 206) | 187 (159, 217) | <0.0001 |
| High density lipoprotein cholesterol [mg/dL] | 39 (32, 48) | 48 (40, 57) | <0.0001 |
| Diabetes mellitus | 156 (23) | 110 (16) | 0.0009 |
| Currently smoking | 237 (35) | 97 (14) | <0.0001 |
| Fatty Acids (% total FA) | | | |
| saturated: | | | |
| Palmitic acid | 22 (21, 24) | 21 (20, 23) | <0.0001 |
| Stearic acid | 14 (13, 16) | 15 (14, 15) | 0.86 |
| monounsaturated: | | | |
| Palmitoleic acid | 1.4 (1.0, 1.9) | 1.3 (1.0, 1.7) | 0.21 |
| Oleic Acid | 18 (15, 20) | 17 (15, 19) | 0.0006 |
| trans unsaturated: | | | |
| trans Palmitoleic acid | 0.42 (0.30, 0.59) | 0.33 (0.23, 0.50) | <0.0001 |
| trans Oleic acid | 2.7 (2.2, 3.2) | 2.4 (1.9, 2.9) | <0.0001 |
| trans, trans linoleic acid | 0.15 (0.11, 0.20) | 0.15 (0.11, 0.19) | 0.06 |
| n-6 polyunsaturated: | | | |
| Linoleic acid | 14 (12, 16) | 16 (15, 18) | <0.0001 |
| γ-Linolenic acid | 0.37 (0.32, 0.42) | 0.43 (0.37, 0.49) | <0.0001 |
| Eicosadienoic acid | 0.25 (0.22, 0.28) | 0.25 (0.22, 0.28) | 0.85 |
| Eicosatrienoic acid | 1.7 (1.5, 2.0) | 1.7 (1.5, 1.9) | 0.31 |
| Arachidonic acid | 14 (12, 17) | 14 (12, 15) | 0.13 |
| Docosapentaenoic acid | 0.61 (0.46, 0.76) | 0.53 (0.41, 0.65) | <0.0001 |
| Docosatetraenoic acid | 2.7 (2.1, 3.5) | 2.5 (2.0, 3.0) | <0.0001 |
| n-3 polyunsaturated: | | | |
| α-Linolenic acid | 0.29 (0.21, 0.40) | 0.44 (0.31, 0.60) | <0.0001 |
| Eicosapentaenoic acid (EPA) | 0.39 (0.30, 0.51) | 0.53 (0.38, 0.85) | <0.0001 |
| Docosapentaenoic acid | 1.7 (1.3, 2.1) | 1.8 (1.5, 2.0) | <0.0001 |
| Docosahexaenoic acid (DHA) | 2.6 (2.0, 3.6) | 3.1 (2.4, 4.5) | <0.0001 |

*Mann-Whitney (Wilcoxon rank-sum) nonparametric test was used for continuous variables, and Chi-square test was used for categorical variables.
†n (%);
‡Median (Inter-quartile range).

TABLE 2

Odds ratios and estimated coefficients from the 10 fatty acids included in the multivariable logistic regression models (per 1 SD; n = 898)

| Variable | Structure | 1 SD (% of total FAs) | Model without CHD risk factors | | | | Model with CHD risk factors | | | |
|---|---|---|---|---|---|---|---|---|---|---|
| | | | Odds Ratio | 95% CI* | Est. ($\beta$) | SE | Odds Ratio | 95% CI* | Est. ($\beta$) | SE |
| Intercept | — | — | — | — | 34.55 | 3.42 | — | — | 7.29 | 2.67 |
| Linoleic acid (n-6) | C18:2 | 2.79 | 0.15 | 0.10 to 0.21 | −1.88 | 0.19 | 0.17 | 0.10 to 0.24 | −1.78 | 0.21 |
| Stearic acid | C18:0 | 1.72 | 0.22 | 0.15 to 0.30 | −1.50 | 0.17 | 0.22 | 0.14 to 0.30 | −1.52 | 0.18 |
| Docosahexaenoic acid (n-3) | C22:6 | 1.50 | 0.33 | 0.23 to 0.41 | −1.12 | 0.13 | 0.37 | 0.26 to 0.48 | −0.99 | 0.14 |
| alpha Linoleic acid (n-3) | C18:3 | 0.23 | 0.35 | 0.24 to 0.48 | −1.04 | 0.16 | 0.32 | 0.21 to 0.44 | −1.13 | 0.16 |
| gamma Linolenic acid (n-6) | C18:3 | 0.10 | 0.42 | 0.29 to 0.56 | −0.87 | 0.13 | 0.46 | 0.31 to 0.62 | −0.78 | 0.14 |
| Palmitoleic acid | C16:1 | 0.69 | 0.43 | 0.27 to 0.63 | −0.85 | 0.21 | 0.43 | 0.25 to 0.67 | −0.85 | 0.24 |
| Aracadonic acid (n-6) | C20:4 | 3.12 | 0.43 | 0.30 to 0.58 | −0.84 | 0.17 | 0.44 | 0.29 to 0.60 | −0.83 | 0.18 |
| trans Palmitoleic acid | trans C16:1 | 1.04 | 0.76 | 0.63 to 0.91 | −0.27 | 0.10 | 0.76 | 0.62 to 0.92 | −0.27 | 0.10 |
| Eicosadienoic acid (n-6) | C20:2 | 0.06 | 1.37 | 1.12 to 1.73 | 0.31 | 0.11 | 1.43 | 1.15 to 1.85 | 0.36 | 0.11 |
| trans Oleic acid | trans C18:1 | 0.84 | 1.37 | 1.06 to 1.82 | 0.31 | 0.12 | 1.32 | 1.02 to 1.78 | 0.27 | 0.12 |
| Male | | | | | | | 0.92 | 0.56 to 1.51 | −0.09 | 0.23 |
| Hypertension | | | | | | | 1.17 | 0.76 to 1.84 | 0.16 | 0.21 |
| Diabetes Mellitus | | | | | | | 0.79 | 0.46 to 1.31 | −0.24 | 0.26 |
| Current Smoker | | | | | | | 2.86 | 1.79 to 5.07 | 1.05 | 0.26 |
| Age (per 10 years) | | | | | | | 1.10 | 0.91 to 1.33 | 0.10 | 0.09 |
| Total Cholesterol† (per 1 SD ≈ 43 mg/dL) | | | | | | | 0.95 | 0.75 to 1.19 | −0.05 | 0.11 |
| HDL† (per 1 SD ≈ 16 mg/dL) | | | | | | | 0.56 | 0.43 to 0.71 | −0.57 | 0.12 |

*95% confidence intervals obtained using bootstrapping method with 10,000 replicates;
†Natural log transformation was modeled.

TABLE 3

Diagnostic characteristics and misclassification error rates of ACS patients and controls

| Model | # Variables in Model | AUC c-statistic | Hosmer-Lemeshow p-value | Positive Likelihood Ratio | Sensitivity (TP) | Specificity (1-FP) | Misclassification Rates (%) | | |
|---|---|---|---|---|---|---|---|---|---|
| | | | | | | | Total | Cases | Controls |
| All Subjects | | | | | | | | | |
| | | | | | | | (n = 450) | (n = 223) | (n = 227) |
| FRS | 7 | 0.77 | 0.30 | 2.5 | 0.70 | 0.72 | 29 | 30 | 28 |
| FA | 10 | 0.85† | 0.01 | 3.2 | 0.79 | 0.75 | 23 | 22 | 25 |
| FRS + FA | 17 | 0.88‡ | 0.22 | 3.8 | 0.83 | 0.78 | 20 | 18 | 22 |
| Statin Naïve Subgroup | | | | | | | | | |
| | | | | | | | (n = 266) | (n = 126) | (n = 140) |
| FRS | 7 | 0.81‡ | 0.15 | 2.9 | 0.73 | 0.75 | 26 | 27 | 25 |
| FA | 10 | 0.86 | 0.00 | 4.1 | 0.83 | 0.80 | 19 | 18 | 20 |
| FRS + FA | 17 | 0.89§ | 0.01 | 4.6 | 0.85 | 0.81 | 15 | 18 | 12 |

FRS, Framingham Risk Score model;
FA, fatty acid model;
FRS + FA, combined model.
†P = 0.003 and
‡P < 0.0002 when compared to FRS (all subjects);
§P = 0.002 when compared to FRS (statin naïve subgroup);
TP, true positive;
FP, false positive;
AUC, area under the receiver operating characteristic curve (c-statistic).
Model calibration: The only models for which calibration was acceptable (i.e., p > 0.05) were those that included the FRS, either alone or when combined with FAs (Table 3).
Model sensitivity and specificity: The positive likelihood ratio for the MLR$_{FRS+FA}$ model was about 50% greater than that for the MLR$_{FRS}$ (Table 3). Sensitivity and specificity were also higher with the combined model, 0.83 and 0.78, respectively.
Model misclassification rate: The overall misclassification rate was 31% lower using the MLR$_{FRS+FA}$ compared to the MLR$_{FRS}$ model (Table 3). When restricted to cases, the MLR$_{FRS+FA}$ misclassification rate was 40% lower.

We herein demonstrated that the FRS has about the same ability to discriminate ACS cases from controls cross-sectionally as it has prospectively (i.e., the c-statistic is 0.7-0.8 in both cases), illustrating the robust character of this metric. More importantly, however, we have demonstrated that a metabolomic approach to ACS case discrimination (whether based on FA profiles or any other small molecules) can significantly and substantially improve ACS case discrimination over standard CHD risk factors. Indeed, blood cell FA profiles were even more powerful than the classic risk factors (cholesterol, blood pressure, diabetes, smoking, etc.) in identifying patients with an ACS.

The relationship between risk for CHD and blood cell levels of individual FAs generally fit well with previous observations: inverse associations with omega-3 and omega-6 FAs and direct associations with trans FAs. However, the ACS discriminatory power of combinations of the FAs described herein is completely unexpected. Of the ten FAs included in the model, increasing levels of eight were inversely associated with odds for ACS case status. These included the FAs of both omega-3 and omega-6 series, the monounsaturated FA palmitoleic acid, and the saturated FA, stearic acid. Direct associations were found only with trans-oleic (or elaidic) acid and eicosadienoic acid. Surprisingly, the FAs that had the greatest impact were the omega-6 FAs, notably linoleic acid, the most common dietary omega-6 FA. Many studies have reported an association between increased intakes and/or in vivo levels of industrially-produced trans FAs and CHD risk[30], whereas little information exists for eicosadienoic acid. It is known to be an intermediate in a secondary biosynthetic pathway to arachidonic acid from linoleic acid[31], and a potential substrate for cyclo-oxygenase[32] but its physiological significance remains to be defined. Several n-6 and n-3 FA-based metrics have been proposed as risk markers in CHD including the omega-3 index[33], the n-6:n3 ratio[26], and the Lands' index[27].

However, in the context of an ACS event, none of these simple prior art FA metrics were able to add to the FRS. In contrast, we discovered that analysis of many blood cell membrane FAs can improve discrimination. Perhaps these other measures would have greater utility in predicting risk for sudden cardiac death[34] than nonfatal CHD events.

One weakness of prior art case controlled studies was that the biomarker measured could be altered by the clinical event it is intended to predict, or having the event can alter behavior which, in turn, alters the biomarker. But these concerns do not appear to apply to blood cell FA profiles of this invention obtained 1-2 days after the onset of ACS, since an MI does not appear to alter these profiles. Siscovick et al. reported that in a study with 18 primates,[13] MI minimally altered red blood cell membrane long chain n-3 FA content, if anything tending to raise, not lower, it. We have confirmed these findings in a rat MI model (Shearer, et al., unpublished observations), and data from others support the view that RBC FA patterns are not materially influenced by an MI.[14,35,36] On these grounds, the FA profiles of this invention here very likely reflected pre-event status suggesting that they could be useful in prospective studies as well.

The discoveries of this invention can be used in the context of diagnosis. To do this, one can include standard diagnostic markers (e.g., creatine kinase MB, cardiac-specific troponin, ECG changes), in blood samples drawn upon admission. Thus, the potential of a FA metabolomic approach for risk prediction, and the value of our findings can be discerned after they have been tested prospectively.

Based on those criteria set forth by Vasan[37] that were addressable with this study design (e.g. discrimination, positive likelihood ratios, misclassification rates, etc.), FA profiles performed well and show promise as a new risk marker for CHD. Although the MLR$_{FA}$ model failed calibration, this was due to the presence of 4 subjects in the control group with FA-based risk scores above the 90$^{th}$ percentile, which was highly predictive of case status. It is possible, however, that these controls could develop an ACS in the future and become cases. Other criteria discussed by Vasan, such as the potential to reveal novel disease mechanisms, also seem to be satisfied since FAs have been shown to impact a variety of pathological processes linked to CHD (inflammation, plaque instability, arrhythmic susceptibility, dyslipidemia, hypertension, etc.). Although we do not wish to be bound by any particular mechanism, these may be in part mediated by alterations in the activity of membrane-associated proteins.[38] Hence, pursuing membrane-mediated mechanisms of disease can lead to new interventional strategies to reduce CHD risk. In addition, since FA profiles can be altered by diet, and such alterations have been shown to reduce risk for CHD[39,40], tracking FA profiles can lead to altered clinical practice, another characteristic of a useful biomarker.

Advantages of this invention include a large sample size, a rigorously-defined ACS population, detailed FA analysis, the use of blood cell membrane FA patterns, and a comprehensive examination of several metrics of model utility. Although this study was conducted in a single metropolitan area and included few minorities, we believe that the approach is applicable to wider populations. The potential for bias existed in the enrollment process as different methods were used to collect demographic and health history data from cases and controls. Although the same questions were asked of both cases and controls the case data were obtained by personal interview and chart review, while control data came from self-filled questionnaires. This could theoretically have led to inaccurate adjustment for covariates, but such a problem would not have altered the relationships between ACS risk and blood cell FA content and would tend to bias our results to the null. A potential exception to this assumption might be that ACS patients who died before enrollment (whether in or out of the hospital), who had dementia or were too ill to interview could theoretically have had even more high-risk FA profiles than the ACS patients enrolled in the study. If so, this would limit the generalizability of the study to "healthier" ACS patients, and our findings would constitute a conservative estimate of the parameter effect sizes in the models tested here. Additionally, unlike cholesterol or blood pressure testing, inter-laboratory standardization does not presently exist for blood cell FA composition (although efforts are currently underway to establish them). Hence, the FA percentages observed here may not be reproducible in other settings using other methods. Finally, we were not able to compare the discriminatory power of FA profiles to that of other known (e.g., current blood pressure, marital status, socio-economic class, exercise) or emerging (e.g., inflammatory markers)[41,42] CHD risk factors, some of which could theoretically modulate or mediate the FA effect. In conclusion, FA profiles added substantially to case discrimination based on the FRS, but more surprisingly, FA profiles alone were able to discriminate ACS cases from controls better than the Framingham model. Thus, without knowledge of serum lipid levels, hypertensive and smoking status, personal/family histories of CHD, or diabetes status, the methods of the present invention alone can be used to predict ACS case status with a relatively high degree of accuracy. These discoveries indicate that the FA-based metabolomic approach to CHD risk assessment of this invention has clinical utility.

Example 2

Using similar methods to those described in Example 1 (except as noted below), we then compared the diagnostic value of combinations of 2 or more fatty acids to the FRS in discriminating cases from controls. In Table 2, the 10-FA marker set has a c-stat=0.85 compared to FRS c-stat=0.77. These numbers considered 450 random subjects selected from the original 1348 patients, since the first ⅔ of the data was used to train the parameter estimates, and then the remaining ⅓ was used to test the misclassification error rates. When all 1348 subject were used to derive c-statistics, the FRS c-stat=0.749 (new Table 4), and this c-stat is compared to the various combinations disclosed below, which all provided improved diagnostic value over the FRS model, as noted in the column labeled 'Difference in c-statistic', which means that the values are the differences in c-statistic compared to the FRS-derived c-statistic.

TABLE 4

Use of fatty acid combinations to discriminate ACS patients from controls (N = 1348)

| Traditional Risk Factors | Area under ROC curve (C-statistic) | Standard Error | Difference in C-statistic |
|---|---|---|---|
| Sex, Age, Hypertension, Diabetes Mellitus, Current Smoker, Total-Chol, HDL-Chol (ie: FRS) | 0.749 | 0.013 | — |
| Fatty Acid Pairs | | | |
| Linoleic, Eicosapentaenoic (EPA) | 0.812 | 0.012 | 0.063 |
| Linoleic, Docosahexaenoic (DHA) | 0.794 | 0.012 | 0.045 |
| Fatty Acid Triplets | | | |
| Linoleic, EPA, gamma-Linolenic | 0.835 | 0.011 | 0.086 |
| Linoleic, DHA, gamma-Linolenic | 0.834 | 0.011 | 0.085 |
| Linoleic, Oleic, gamma-Linolenic | 0.823 | 0.011 | 0.074 |
| Linoleic, EPA, alpha-Linolenic (ALA) | 0.823 | 0.011 | 0.074 |
| Linoleic, n-3 docosapentaenoic (n-3 DPA), gamma-Linolenic | 0.822 | 0.011 | 0.073 |
| Linoleic, EPA, Palmitic | 0.822 | 0.011 | 0.073 |
| Linoleic, EPA, Stearic | 0.822 | 0.011 | 0.073 |
| Linoleic, EPA, Elaidic | 0.818 | 0.012 | 0.069 |
| Oleic, ALA, gamma-Linolenic | 0.818 | 0.012 | 0.069 |
| Linoleic, EPA, n-6 docosapentaenoic (n-6 DPA) | 0.818 | 0.012 | 0.069 |
| Oleic, Docosatetraenoic (DTA), gamma-Linolenic | 0.817 | 0.012 | 0.068 |
| Linoleic, EPA, DTA | 0.817 | 0.012 | 0.068 |
| Elaidic, Palmitic, ALA | 0.816 | 0.012 | 0.067 |
| Linoleic, EPA, Arachidonic (AA) | 0.816 | 0.012 | 0.067 |
| Linoleic, EPA, Oleic | 0.815 | 0.012 | 0.066 |
| Linoleic, DHA, ALA | 0.813 | 0.012 | 0.064 |
| Linoleic, DHA, EPA | 0.813 | 0.012 | 0.064 |
| Linoleic, EPA, n-3 DPA | 0.812 | 0.012 | 0.063 |
| Palmitic, EPA, ALA | 0.810 | 0.012 | 0.061 |
| EPA, Palmitic, gamma-Linolenic | 0.809 | 0.012 | 0.060 |
| EPA, ALA, gamma-Linolenic | 0.807 | 0.012 | 0.058 |
| EPA, Oleic, gamma-Linolenic | 0.807 | 0.012 | 0.058 |
| DHA, ALA, gamma-Linolenic | 0.806 | 0.012 | 0.057 |
| Oleic, n-6 DPA, gamma-Linolenic | 0.806 | 0.012 | 0.057 |
| Linoleic, DHA, Elaidic | 0.804 | 0.012 | 0.055 |
| Oleic, AA, gamma-Linolenic | 0.804 | 0.012 | 0.055 |
| Palmitic, DTA, gamma-Linolenic | 0.802 | 0.012 | 0.053 |
| ALA, Palmitic, gamma-Linolenic | 0.801 | 0.012 | 0.052 |
| EPA, Palmitoleic, gamma-Linolenic | 0.801 | 0.012 | 0.052 |
| Linoleic, ALA, n-3 DPA | 0.800 | 0.012 | 0.051 |
| Linoleic, Stearic, gamma-Linolenic | 0.800 | 0.012 | 0.051 |
| Linoleic, Palmitic, gamma-Linolenic | 0.800 | 0.012 | 0.051 |
| Linoleic, Stearic, DHA | 0.800 | 0.012 | 0.051 |
| Linoleic, Palmitic, DHA | 0.800 | 0.012 | 0.051 |
| Linoleic, Elaidic, Palmitic | 0.800 | 0.012 | 0.051 |
| ALA, Palmitic, DTA | 0.799 | 0.012 | 0.050 |
| Linoleic, ALA, Palmitic | 0.798 | 0.012 | 0.049 |
| Linoleic, DHA, Palmitoleic | 0.796 | 0.012 | 0.047 |
| Linoleic, DHA, cis-11,14-Eicosadienoic | 0.796 | 0.012 | 0.047 |
| Linoleic, DHA, n-3 DPA | 0.795 | 0.012 | 0.046 |
| Linoleic, DHA, Oleic | 0.795 | 0.012 | 0.046 |
| Linoleic, DHA, AA | 0.795 | 0.012 | 0.046 |
| Linoleic, ALA, Oleic | 0.795 | 0.012 | 0.046 |
| DHA, Oleic, gamma-Linolenic | 0.794 | 0.012 | 0.045 |

*All p-values <= 0.01.

REFERENCES

1. Assmann G, Cullen P, Schulte H. Simple scoring scheme for calculating the risk of acute coronary events based on the 10-year follow-up of the prospective cardiovascular Munster (PROCAM) study. *Circulation*. 2002; 105(3):310-315.
2. De Backer G, Ambrosioni E, Borch-Johnsen K, Brotons C, Cifkova R, Dallongeville J, Ebrahim S, Faergeman O, Graham I, Mancia G, Cats V M, Orth-Gomer K, Perk J, Pyorala K, Rodicio J L, Sans S, Sansoy V, Sechtem U, Silber S, Thomsen T, Wood D. European guidelines on cardiovascular disease prevention in clinical practice. Third Joint Task Force of European and other Societies on Cardiovascular Disease Prevention in Clinical Practice (constituted by representatives of eight societies and by invited experts). *Atherosclerosis*. 2004; 173(2):381-391.
3. Chambless L E, Folsom A R, Sharrett A R, Sorlie P, Couper D, Szklo M, Nieto F J. Coronary heart disease risk prediction in the Atherosclerosis Risk in Communities (ARIC) study. *Journal of clinical epidemiology*. 2003; 56(9):880-890.
4. Executive Summary of The Third Report of The National Cholesterol Education Program (NCEP) Expert Panel on Detection, Evaluation, And Treatment of High Blood Cholesterol In Adults (Adult Treatment Panel III). *Jama*. 2001; 285(19):2486-2497.
5. Wilson P W, D'Agostino R B, Levy D, Belanger A M, Silbershatz H, Kannel W B. Prediction of coronary heart disease using risk factor categories. *Circulation*. 1998; 97(18):1837-1847.
6. Myerburg R J, Kessler K M, Castellanos A. Sudden cardiac death: epidemiology, transient risk, and intervention assessment. *Annals of internal medicine*. 1993; 119(12):1187-1197.
7. Grewal J, Anand S, Islam S, Lonn E. Prevalence and predictors of subclinical atherosclerosis among asymptomatic "low risk" individuals in a multiethnic population. *Atherosclerosis*. 2008; 197(1):435-442.
8. Lloyd-Jones D M, Liu K, Tian L, Greenland P. Narrative Review: Assessment of C-Reactive Protein in Risk Prediction for Cardiovascular Disease. *Annals of internal medicine*. 2006.
9. Folsom A R, Chambless L E, Ballantyne C M, Coresh J, Heiss G, Wu K K, Boerwinkle E, Mosley T H, Jr., Sorlie P, Diao G, Sharrett A R. An assessment of incremental coronary risk prediction using C-reactive protein and other novel risk markers: the atherosclerosis risk in communities study. *Archives of internal medicine*. 2006; 166(13):1368-1373.
10. Block R C, Harris W S, Reid K J, Sands S A, Spertus J A. EPA and DHA in blood cell membranes from acute coronary syndrome patients and controls. *Atherosclerosis*. 2007.
11. Harris W S, Poston W C, Haddock C K. Tissue n-3 and n-6 fatty acids and risk for coronary heart disease events. *Atherosclerosis*. 2007; 193(1):1-10.
12. Albert C M, Campos H, Stampfer M J, Ridker P M, Manson J E, Willett W C, Ma J. Blood levels of long-chain n-3 fatty acids and the risk of sudden death. *The New England journal of medicine*. 2002; 346(15):1113-1118.
13. Siscovick D S, Raghunathan T E, King I, Weinmann S, Wicklund K G, Albright J, Bovbjerg V, Arbogast P, Smith H, Kushi L H, et al. Dietary intake and cell membrane levels of long-chain n-3 polyunsaturated fatty acids and the risk of primary cardiac arrest. *Jama*. 1995; 274(17):1363-1367.
14. Kark J D, Manor O, Goldman S, Berry E M. Stability of red blood cell membrane fatty acid composition after acute myocardial infarction. Journal of clinical epidemiology. 1995; 48(7):889-895.

15. German J B, Gillies L A, Smilowitz J T, Zivkovic A M, Watkins S M. Lipidomics and lipid profiling in metabolomics. *Current opinion in lipidology.* 2007; 18(1):66-71.
16. Cook N R. Use and misuse of the receiver operating characteristic curve in risk prediction. *Circulation.* 2007; 115(7):928-935.
17. Cook N R. Statistical evaluation of prognostic versus diagnostic models: beyond the ROC curve. *Clinical chemistry.* 2008; 54(1):17-23.
18. Greenland P. Comments on 'Evaluating the added predictive ability of a new marker: From area under the ROC curve to reclassification and beyond' by M. J. Pencina, R. B. D'Agostino Sr, R. B. D'Agostino Jr, R. S. Vasan, Statistics in Medicine (DOI: 10.1002/sim.2929). *Statistics in medicine.* 2008; 27(2):188-190.
19. Pencina M J, D'Agostino R B S, D'Agostino R B J, Vasan R S. Evaluating the added predictive ability of a new marker: From area under the ROC curve to reclassification and beyond. *Statistics in medicine.* 2008; 27(2):157-172.
20. Pepe M S, Janes H, Longton G, Leisenring W, Newcomb P. Limitations of the odds ratio in gauging the performance of a diagnostic, prognostic, or screening marker. *American journal of epidemiology.* 2004; 159(9):882-890.
21. Lemley K V. An introduction to biomarkers: applications to chronic kidney disease. *Pediatric nephrology (Berlin, Germany).* 2007; 22(11):1849-1859.
22. Alpert J S, Thygesen K, Antman E, Bassand J P. Myocardial infarction redefined—a consensus document of The Joint European Society of Cardiology/American College of Cardiology Committee for the redefinition of myocardial infarction. *Journal of the American College of Cardiology.* 2000; 36(3):959-969.
23. Braunwald E, Antman E M, Beasley J W, Califf R M, Cheitlin M D, Hochman J S, Jones R H, Kereiakes D, Kupersmith J, Levin T N, Pepine C J, Schaeffer J W, Smith E E, 3rd, Steward D E, Theroux P, Gibbons R J, Alpert J S, Faxon D P, Fuster V, Gregoratos G, Hiratzka L F, Jacobs A K, Smith S C, Jr. ACC/AHA 2002 guideline update for the management of patients with unstable angina and non-ST-segment elevation myocardial infarction—summary article: a report of the American College of Cardiology/American Heart Association task force on practice guidelines (Committee on the Management of Patients With Unstable Angina). *Journal of the American College of Cardiology.* 2002; 40(7): 1366-1374.
24. Lanfear D E, Jones P G, Marsh S, Cresci S, McLeod H L, Spertus J A. Beta2-adrenergic receptor genotype and survival among patients receiving beta-blocker therapy after an acute coronary syndrome. *Jama.* 2005; 294(12):1526-1533.
25. Harris W S. Omega-3 fatty acids and cardiovascular disease: a case for omega-3 index as a new risk factor. *Pharmacol Res.* 2007; 55(3):217-223.
26. Harris W S. The omega-6/omega-3 ratio and cardiovascular disease risk: uses and abuses. *Current atherosclerosis reports.* 2006; 8(6):453-459.
27. Lands W E. Long-term fat intake and biomarkers. *The American journal of clinical nutrition.* 1995; 61(3 Suppl): 721S-725S.
28. Hanley J A, McNeil B J. The meaning and use of the area under a receiver operating characteristic (ROC) curve. *Radiology.* 1982; 143(1):29-36.
29. Hanley J A, McNeil B J. A method of comparing the areas under receiver operating characteristic curves derived from the same cases. *Radiology.* 1983; 148(3):839-843.
30. Willett W C. Trans fatty acids and cardiovascular disease-epidemiological data. *Atheroscler Suppl.* 2006; 7(2):5-8.
31. Marcel Y L, Christiansen K, Holman R T. The preferred metabolic pathway from linoleic acid to arachidonic acid in vitro. *Biochimica et biophysica acta.* 1968; 164(1):25-34.
32. Koshkin V, Dunford H B. Reaction of prostaglandin endoperoxide synthase with cis,cis-eicosa-11,14-dienoic acid. *The Journal of biological chemistry.* 1998; 273(11): 6046-6049.
33. Harris W S, Von Schacky C. The Omega-3 Index: a new risk factor for death from coronary heart disease? *Preventive medicine.* 2004; 39(1):212-220.
34. Harris W S, von Schacky C. Omega-3 Fatty Acids, Acute Coronary Syndrome, and Sudden Death. *Current Cardiovascular Risk Reports.* 2008; 2:161-166.
35. Jurand J, Oliver M F. Effects of acute myocardial infarction and of noradrenaline infusion on fatty acid composition of serum lipids. *Atherosclerosis.* 1970; 11(1):157-170.
36. Maidment C G, Jones S P, Lea E J. Changes in platelet membrane fatty acids after myocardial infarction. *Atherosclerosis.* 1988; 74(1-2):9-14.
37. Vasan R S. Biomarkers of cardiovascular disease: molecular basis and practical considerations. *Circulation.* 2006; 113(19):2335-2362.
38. Ma D W, Seo J, Switzer K C, Fan Y Y, McMurray D N, Lupton J R, Chapkin R S. n-3 PUFA and membrane microdomains: a new frontier in bioactive lipid research. *The Journal of nutritional biochemistry.* 2004; 15(11):700-706.
39. Wang C, Harris W S, Chung M, Lichtenstein A H, Balk E M, Kupelnick B, Jordan H S, Lau J. n-3 Fatty acids from fish or fish-oil supplements, but not alpha-linolenic acid, benefit cardiovascular disease outcomes in primary- and secondary-prevention studies: a systematic review. *The American journal of clinical nutrition.* 2006; 84(1):5-17.
40. Marchioli R, Barzi F, Bomba E, Chieffo C, Di Gregorio D, Di Mascio R, Franzosi M G, Geraci E, Levantesi G, Maggioni A P, Mantini L, Marfisi R M, Mastrogiuseppe G, Mininni N, Nicolosi G L, Santini M, Schweiger C, Tavazzi L, Tognoni G, Tucci C, Valagussa F. Early protection against sudden death by n-3 polyunsaturated fatty acids after myocardial infarction: time-course analysis of the results of the Gruppo Italiano per lo Studio della Sopravvivenza nell'Infarto Miocardico (GISSI)-Prevenzione. *Circulation.* 2002; 105(16): 1897-1903.
41. Niu K, Hozawa A, Kuriyama S, Ohmori-Matsuda K, Shimazu T, Nakaya N, Fujita K, Tsuji I, Nagatomi R. Dietary long-chain n-3 fatty acids of marine origin and serum C-reactive protein concentrations are associated in a population with a diet rich in marine products. *The American journal of clinical nutrition.* 2006; 84(1):223-229.
42. Ferrucci L, Cherubini A, Bandinelli S, Bartali B, Corsi A, Lauretani F, Martin A, Andres-Lacueva C, Senin U, Guralnik J M. Relationship of plasma polyunsaturated fatty acids to circulating inflammatory markers. *The Journal of clinical endocrinology and metabolism.* 2006; 91(2): 439-446.

We claim:
1. A method for predicting the risk of acute coronary syndrome (ACS) in a human subject, comprising:
   (a) measuring, in a fatty acid sample isolated from red blood cells from a human subject, an amount of:
      (i) linoleic acid and gamma-linolenic acid; and
      (ii) docosahexaenoic acid (DHA) and optionally eicosapentaenoic acid (EPA);

(b) comparing the amount of (a)(i) and (a)(ii) in the fatty acid sample to an amount of (a)(i) and (a)(ii) in a control; and (c) predicting a risk of ACS, wherein the amount of each of the fatty acids measured in (a) is inversely correlated with the risk of ACS.

2. The method of claim 1, wherein the measuring comprises measuring an amount of linoleic acid, gamma-linolenic acid, DHA, and EPA in the fatty acid sample.

3. The method of claim 1, further comprising (d) measuring an amount of one or more fatty acids selected from the group consisting of alpha-linolenic acid, palmitic acid, stearic acid, trans-oleic acid, n-6 docosapentaenoic acid, docosatetraenoic acid, arachidonic acid, oleic acid, n-3 docosapentaenoic acid, palmitoleic acid, trans-palmitoleic acid, and eicosadienoic acid in the fatty acid sample;

(e) comparing the amount the one or more fatty acids selected from the group to an amount of the one or more fatty acids selected from the group in the control; and (f) using the comparison in step (e) in the predicting the risk of ACS.

4. The method of claim 1 further comprising (d) measuring an amount of one or more fatty acids selected from the group consisting of stearic acid, alpha-linoleic acid, palmitoleic acid, arachidonic acid, trans-palmitoleic acid, eicosadienoic acid and trans-oleic acid in the fatty acid sample;

(e) comparing the amount of the one or more fatty acids measured in step (d) to an amount of the one or more fatty acids selected from the group in the control; and (f) using the comparison in step (e) in the predicting the risk of ACS.

5. The method of claim 1, further comprising (d) measuring an amount of one or more fatty acids selected from the group consisting of alpha-linolenic acid, palmitic acid, stearic acid, trans-oleic acid, n-6 docosapentaenoic acid, docosatetraenoic acid, arachidonic acid, oleic acid, n-3 docosapentaenoic acid, palmitoleic acid, trans palmitoleic, and eicosadienoic acid in the fatty acid sample; and (e) comparing the amount the one or more fatty acids measured in step (d) to an amount of the one or more fatty acids in the control; and (f) using the comparison in step (e) in the predicting the risk of ACS.

6. The method of claim 1, further comprising (d) measuring an amount of one or more fatty acids selected from the group consisting of palmitic acid, alpha-linolenic acid, oleic acid and palmitoleic acid in the fatty acid sample; and (e) comparing the amount the one or more fatty acids measured in step (d) to an amount of the one or more fatty acids in the control; and (f) using the comparison in step (e) in the predicting the risk of ACS.

7. The method of claim 1, wherein the measuring comprises measuring a percent total of the (a)(i) fatty acids and the (a)(ii) fatty acids in the fatty acid sample as a percent of total fatty acids in the fatty acid sample.

8. The method of claim 7, wherein comparing the amount of the one or more fatty acids to a control comprises (a) multiplying the percent total of the (a)(i) fatty acids and the (a)(ii) fatty acids in the fatty acid sample by a predetermined weighting coefficient to produce an individual fatty acid score; and (b) summing the individual fatty acid scores to produce a risk score, wherein the risk score is used to correlate with ACS in the human subject.

9. The method of claim 7, further comprising subjecting the percent total of the (a)(i) fatty acids and the (a)(ii) fatty acids in the fatty acid sample to an analysis selected from the group consisting of generalized models, multivariate analysis, and time-to-event survival analysis, to produce a modified risk score; wherein the modified risk score is used to correlate with ACS in the human subject.

10. The method of claim 1, further comprising determining a Framingham risk score for the subject.

11. The method of claim 1, wherein the subject has a family history of ACS, a genetic predisposition to ACS, and/or has previously suffered from ACS.

12. The method of claim 1 wherein the acute coronary syndrome is myocardial infarction or unstable angina.

13. A method for predicting the risk of acute coronary syndrome (ACS) in a human subject, comprising:

(a') identifying a combination of fatty acids that discriminate the ACS cases from a control, said combination of fatty acids comprising linoleic acid, alpha-linolenic acid, arachidonic acid, eicosapentaenoic acid (EPA), and docosahexaenoic acid (DHA);

(a) measuring, in a fatty acid sample isolated from red blood cells from a subject, an amount comprising the fatty acids identified in (a');

(b) comparing the amount of (a) in the fatty acid sample to an amount of (a) in a control; and (c) predicting a risk of ACS.

14. The method of claim 1, wherein the measuring further comprises measuring an amount of alpha-linolenic acid and arachidonic acid in the fatty acid sample.

15. The method of claim 1, wherein the measuring further comprises measuring an amount of stearic acid, alpha-linoleic acid, palmitoleic acid, arachidonic acid, trans-palmitoleic acid, eicosadienoic acid and trans-oleic acid in the fatty acid sample.

16. The method of claim 13, wherein the combination of fatty acids identified in (a') further comprises stearic acid, palmitoleic acid, trans-palmitoleic acid, eicosadienoic acid and trans-oleic acid.

* * * * *